United States Patent [19]
McMahon

[11] Patent Number: 6,088,657
[45] Date of Patent: Jul. 11, 2000

| [54] | PORTABLE HAY BALE MOISTURE TESTER |
|---|---|
| [75] | Inventor: Michael T. McMahon, Salem, Ohio |
| [73] | Assignee: Farmex, Inc., Aurora, Ohio |
| [21] | Appl. No.: 09/000,747 |
| [22] | Filed: Dec. 30, 1997 |
| [51] | Int. Cl.[7] ................................................. G01R 27/02 |
| [52] | U.S. Cl. .............................. 702/50; 73/73; 324/694; 340/604 |
| [58] | Field of Search ............... 702/50; 324/694, 324/696, 724; 73/73; 340/604 |

[56] References Cited

U.S. PATENT DOCUMENTS

| 4,451,781 | 5/1984 | Anderson | 324/694 |
|---|---|---|---|
| 4,812,741 | 3/1989 | Stowell | 324/694 |
| 4,868,491 | 9/1989 | Black | 324/694 |
| 4,954,783 | 9/1990 | Spry | 324/696 |

Primary Examiner—Marc S. Hoff
Assistant Examiner—Hien Vo
Attorney, Agent, or Firm—Vytas R. Matas

[57] ABSTRACT

A hay bale moisture measuring device comprising a bimetalic, probe forming a single cell battery uses the hay and the moisture therein as the electrolytes to provide an internal cell resistance measurement which is calculated in an electronic circuit according to a predetermined algorithm into a hay moisture measurement which is further biased for hay temperature, bale configuration, hay type, cutting and density by the same circuit.

28 Claims, 5 Drawing Sheets

PORTABLE HAY BALE MOISTURE TESTER

BACKGROUND OF THE INVENTION

1. Field of the Invention

The present invention relates to hay moisture testers or meter assemblies generally and more particularly to portable hay moisture testers or meters providing a wide range of detectable hay moisture levels with compensation for different hay conditions and varieties

2. Description of the Prior Art

If hay is too wet it can mold and lose nutritional value. If it is determined that the hay is too wet to bale, the farmer may elect to harvest the hay at a later time allowing the hay to dry further. Or he may elect to harvest the hay in the form of sileage as opposed to bales or spray preservatives to the hay to prevent mold. If the hay is too dry, the leaves tend to dry and crumble when baled thus making the farmer suffer from a lower yield. Thus portable hay moisture testing is used by the farmer to check on the condition of the hay allowing him to make an informed decision as to the proper treatment of the hay.

Known portable hay moisture testers utilize the electrical conductivity of the hay to determine the moisture within the hay. Such devices determine the moisture content of the hay by measuring the electrical conductivity of the hay, which varies in direct proportion to the moisture level of the hay.

One problem with such known hay moisture testers implementing the electrical conductivity principle is their limited response with wet hay above 40% moisture. Such wet hay tends to short-circuit the measuring device. Therefore hay will not increase the level of conductivity having additional moisture content above this 40% level making such measurements impossible.

The mentioned prior art devices in some cases also provided a limited digital display of the moisture content of the tested hay bales. These displays were limited to the moisture reading and did not provide any further information as to the conditions under which the measurement was made. Information such as a full text complementary digital readout of the hay bale type (round or square), the hay cutting (first, second, third, etc), or the density of the hay bale was not provided.

These known instruments also failed to compensate for the type of hay bale being tested which factors will influence the accuracy of the moisture tester measurement. Round bales of hay are generally wrapped much tighter and compacted differently from square bales and will yield a much higher reading on the moisture tester than the equivalent square bale of the same moisture level. None of the known moisture testers allow for the tester to be biased by the user to compensate for the measurement being taken on either a round or square bale of hay.

The cutting of the hay can also influence the accuracy of the moisture tester measurement. For example, the leaf to stem ratio of the particular hay crop can vary as a function of the seasonal cutting which ratio results in different moisture readings for the hay measured. The second cutting typically yields better alfalfa quality then the first, the third cutting typically yields better quality then the second, and so on. None of the know moisture testers provide for the tester to be biased by the user to compensate for the seasonal cutting of the measured hay.

The density of the measured hay bale will also influence the accuracy of a moisture tester. If a given bale is of a loose density, the moisture reading of the tester will indicate a lower moisture than it otherwise would if the bale were of a more normal density. Likewise, if a given bale is of a tighter density, the moisture reading of the tester will indicate a higher moisture than it otherwise would if the bale were of a more normal density. None of the known moisture testers provide for the tester to be biased by the user to compensate for the density variations of the hay measured.

The type of hay will also significantly influence the accuracy of the moisture tester measurement. Alfalfa hay, for example, will give a different measurement than timothy hay when both the alfalfa and the timothy are at the same moisture level. None of the known moisture testers provide for the tester to be biased by the user to compensate for the type of hay being tested.

Thus what the hay harvesting industry needed a portable hay moisture tester having a wide range of moisture measurements and providing compensation for differing hay types and bale conditions.

BRIEF SUMMARY OF THE INVENTION

The present invention solves the problems associated with known portable hay moisture testers as well as others by providing a portable hay moisture tester having a wide range of moisture measurement exceeding 40% and providing built in compensation for hay type and condition. To accomplish this end applicants' tester implements a very different measuring approach based on the construction of a bimetallic probe having the two differing material conductors separated by an insulator which then uses the hay and the associated moisture in the hay as an electrolyte to form a single cell battery. Two different metal conductors separated by an insulator are used to construct this bimetallic probe. One metal electrode acts as an anode and the second metal electrode acts as a cathode of the mentioned single cell battery. When the bimetallic probe is inserted into a hay bale, the hay and the moisture in the hay act as an electrolyte. Thus a voltage or an Electro Motive Force (EMF) is generated across the anode and cathode and a battery cell is formed. The internal resistance of this battery cell is inversely proportional to the moisture in the hay. An electronic circuit controlled by a microprocessor, places fixed load resistance across the mentioned probe cell and the microprocessor mathematically determines according to a predetermined formula the moisture within the hay bale from the measured electronic signal which is indicative of the internal resistance of the formed cell. The cell is not short-circuited by hay moisture in excess of 40% and thus provides a wide range of hay moisture measurements.

The moisture measured is accomplished by first measuring the open circuit voltage of the mentioned single cell battery. Then a fixed load resistance is placed across the single cell battery and again the cell voltage with the loaded condition is measured. The internal resistance of the battery can now be determined. The greater the moisture content of the hay, the smaller the value of the internal resistance of the cell. The moisture content of the hay in the present invention is determined by a measurement that is indicative of the internal resistance of the battery. The moisture content of the hay is determined by measuring the change in cell voltage as a function of fixed loads since the change in cell voltage from no load to a known fixed load condition is directly proportional to the internal resistance of the cell.

The portable tester of the present invention also provides the operator with the capability to:

1) Select and compensate for the bale type (round or square).

2) Select and compensate for the hay cutting (first, second, third, etc).

3) Select and compensate for the hay type (alfalfa, timothy, grass, etc.).

4) Bias and compensate for the relative hay density.

5) Activate/deactivate a backlight for a sixteen-character display.

6) Access, display and select via a "Menu" switch the bale type, hay cutting, hay type and hay density options.

The present invention also solves problems associated with the measuring temperature of the probe cell. The hay moisture signal varies with the temperature of the hay bale. A temperature sensor is mounted in the probe of the tester such that when the probe is inserted into the hay bale, the temperature of the hay bale is measured and this measurement provided to a microprocessor that biases the moisture reading mathematically according to calculations performed by the microprocessor.

The tester of the present invention also provides a large sixteen character alphanumeric display with back light display capability for easy visibility for low light viewing.

The sixteen character display allows the operator to select in full text:

1) Bale type (round or square).
2) Hay cutting (first, second, third, etc . . . ).
3) Hay type (alfalfa, timothy, grass, etc . . . ).
4) Hay density.

The same sixteen character display further allows the operator to display the moisture of the hay, the temperature of the hay, and the average, minimum and maximum moisture readings for a sequence of tests on a given hay bale.

In view of the foregoing it will be seen that one aspect of the present invention is to provide a portable hay moisture meter having a bimetallic probe using the bimetal to act as the plates of a battery and using the hay and associated moisture within the hay to act as the electrolyte of the said battery to provide battery EMF signal varying with the hay moisture level.

Another aspect of the invention is to provide a calibration technique of measuring the internal resistance of the above described battery via a circuit that yields a signal that is in turn is indicative of the internal resistance, where the moisture content of the hay is inversely proportional to the internal resistance of the battery.

Another aspect of the invention is to provide a hay moisture tester having a sixteen character digital display, which can sequentially display for selection preprogrammed hay variable parameters to compensate for measurement affecting variables associated with the hay measurement including the bale type, hay cutting, hay type and hay density.

Yet another aspect of the present invention is to provide a hay moisture tester having a temperature compensation circuit with the temperature sensor mounted in a probe tip of the tester, allowing for microprocessor controlled automatic temperature compensation of the hay bale.

Still yet another aspect of the present invention is to provide a backlighted sixteen character alphanumeric display on a portable hay moisture meter to allow field use of the device in low light conditions.

A further aspect of the present invention is to provide the hay moisture tester with a pushbutton referred to as 'Menu' that allows the user to directly access and select preprogrammed options for the bale type, hay cutting, hay type, and hay density.

Still a further aspect of the present invention is to provide a portable hay moisture meter which will retain via an EEPROM all of its variable compensation selections including, bale type, hay cutting, hay type and hay density, when the unit is turned off or if the batteries should fail or be removed.

These and other aspects of the present invention will be more fully understood from a review of the following detailed description of the preferred embodiment of the invention when considered in junction with the accompanying drawings.

DETAILED DESCRIPTION OF THE PREFERRED EMBODIMENT

Figure 1:
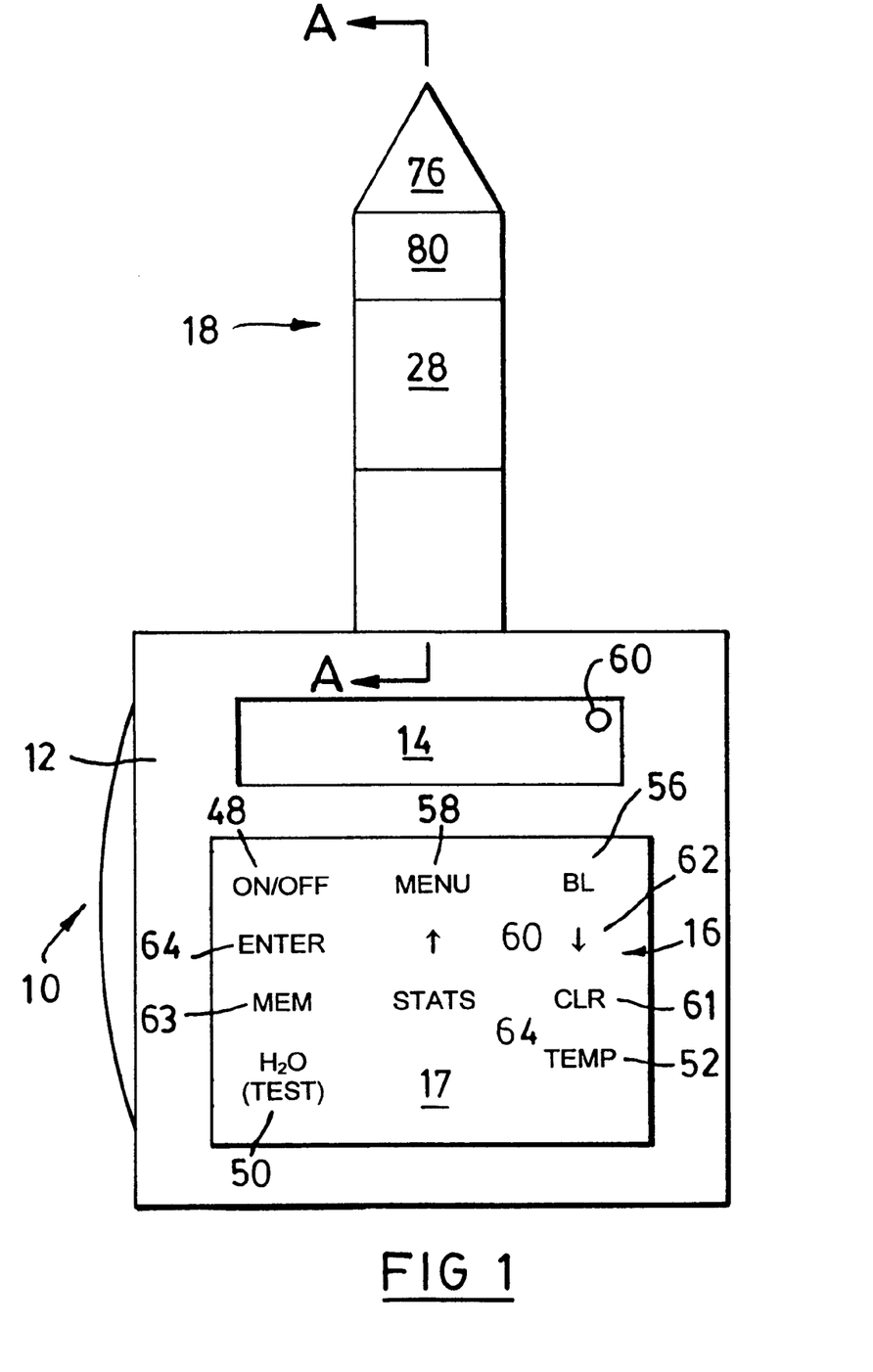
FIG. 1 is a side view of the portable hay moisture tester of the present invention showing the back lighted sixteen character digital display along with accompanying control buttons, and the bimetallic probe.

Referring now to the drawings generally and with particular reference to FIG. 1, a portable hay moisture meter or tester (10) is shown having a top panel assembly (12) which includes a sixteen character digital alphanumeric display panel (14) which when actuated provides information regarding the hay testing procedure through a series of operator actuated switches (16) depicted on a pressure sensitive membrane (17) of known construction and operation.

Some of the membrane switches (16) serve dual functions and therefore have two distinct functions depicted on the switch face. The statistical function switches 'M', 'STATS', and 'CLR' are depicted below the menu function switches 'ENTER', 'UP ARROW' and "DOWN ARROW' respectively.

The moisture meter (10) is an Electro Motive Force type meter, herein referred to as an EMF meter, utilizing the hay and associated moisture within the hay to provide the electrolytic component which together with the bimetallic probe assembly (18) forms a type of single cell battery. The moisture in the hay, forming the majority of the electrolyte, determines the internal resistance of the single cell battery. An electronic circuit that yields a signal indicative of the internal resistance of said cell, is read by a microprocessor (58). The microprocessor (58) in turn calculates the moisture of the hay.

Figure 2:
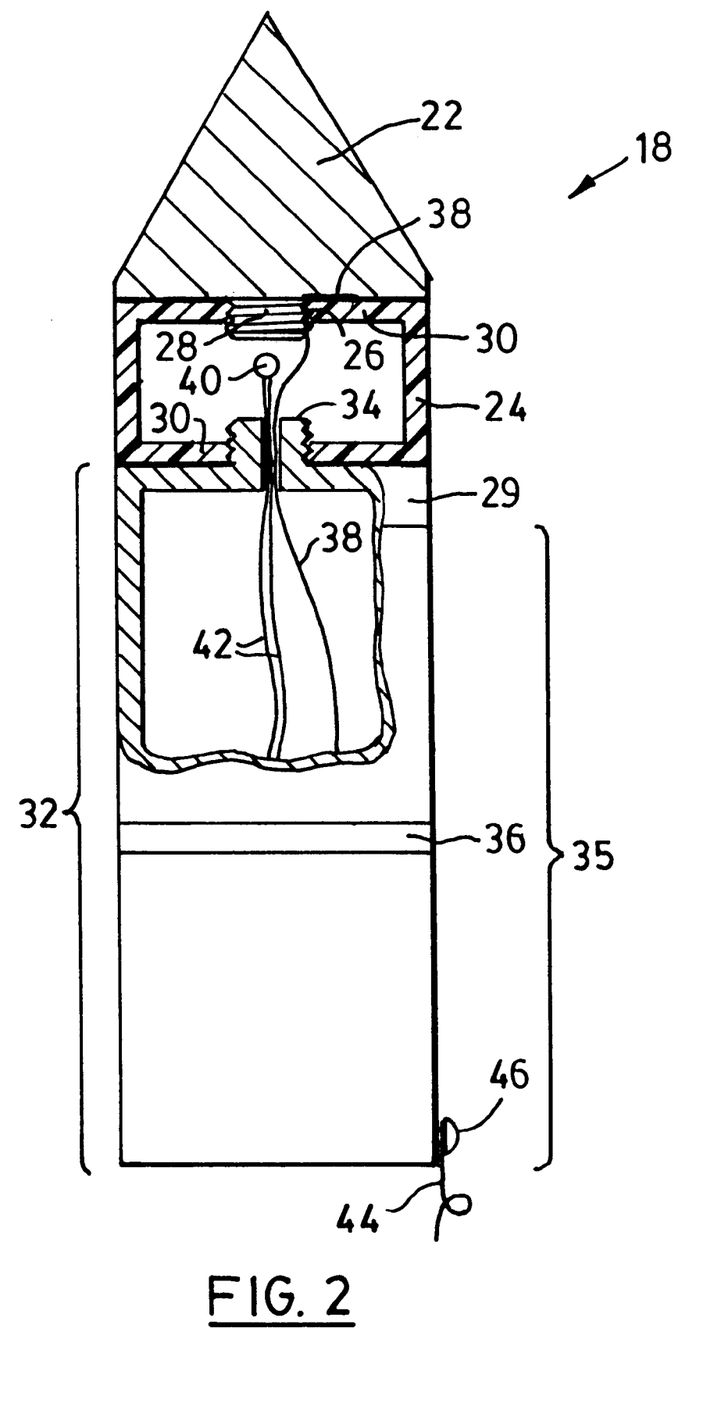
FIG. 2 is a cut away sectional view of the bimetallic probe of the portable hay moisture tester of FIG. 1 taken along section A-A.
Figure 3:
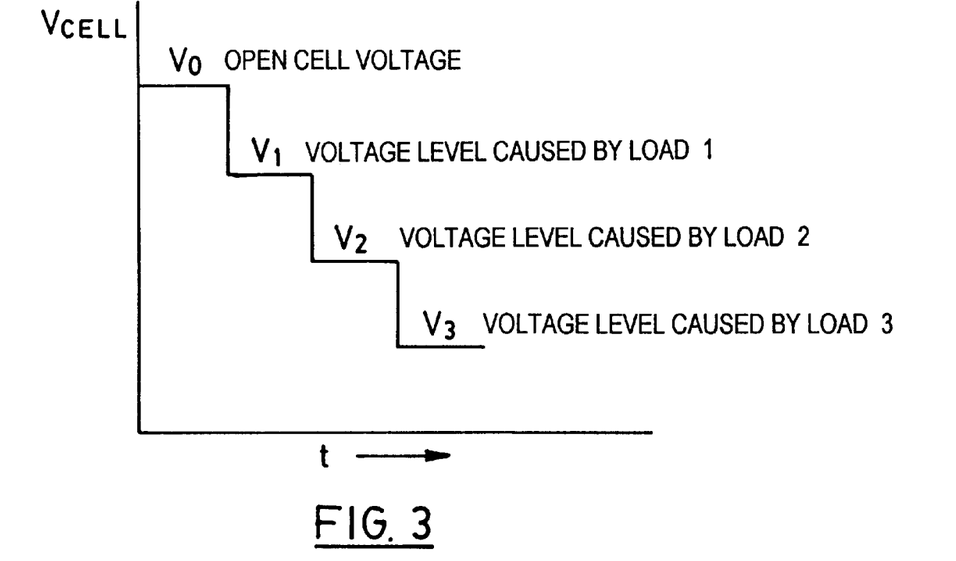
FIG. 3 is a calibration graph of the EMF output of the tester of FIG. 1 when subjected to different load levels.

Referring now to FIG. 2, it will be seen that the probe assembly (18) is constructed by attaching a brass pointed component (22) to a hollow insulator tube (24) by complementary threads (26) formed on an end (28) of the brass component (22) and in a solid end (30) of the insulator tube (24). The other end of the insulator tube (24) is attached to a probe main shaft (32) by a threaded extension (34) screwed into the solid end (30) of the insulator tube (24). The pointed brass component (22) acts as one of the bimetallic cell plates. The probe shaft (32) is hollow and is constructed of aluminum and consists of a large anodized aluminum section (35) with a small unanodized position indicator band (36) and an unanodized section (29). The large anodized section (35) acts as an insulator while the unanodized section (29) acts as the second bimetallic cell plate. The unanodized section (29) is of a fixed length so as to control the geometry of the sensing area.

A wire (38) is physically and electrically secured to the brass component (22) of the bimetallic probe (18) by jamming the wire strands between the complementary threads (26) when the brass component (22) is fastened to the insulator (24) by screwing the threaded top (28) into the complimentary threads of the insulator (24).

A temperature sensing diode (40) with two associated lead wires (42) is located in the hollow probe shaft (32) with the temperature sensing diode (40) in close proximity to the insulator (24) and the high thermal conductivity brass component tip (22).

A shaft wire (44) is physically and electrically secured to the probe shaft (32) by means of a sheet metal screw (46), which is used to electrically connect the probe (18) to the body of the moisture tester (10).

A moisture measurement is achieved by inserting the metallic probe (18) perpendicularly into the hay bale until the desired position indicator band (36) is flush with the surface of the exterior plane of the hay bale. This feature allows for repeatability in penetrating a hay bale to a fixed depth and therefore sensing the moisture of the bale at a fixed depth.

Once the probe is inserted into the hay bale, moisture testing of the same may be initiated. The moisture meter (10) is portable and hence battery operated. To power the device, an on/off switch (48) is pressure activated to connect a battery to the electrical circuitry of the meter (10).

With the meter (10) activated, the digital display (14) will display a message such as 'Ready', indicting that the said meter is powered and waiting for further operator action. With the unit (10) activated the operator may initiate a moisture measurement by depressing the moisture test button (50). At the completion of the moisture measurement the moisture meter (10) will indicate the moisture content of the hay on the sixteen character display (14). Additionally, the operator may initiate a temperature measurement of the hay by depressing a temperature test button (52). At the completion of the temperature measurement the moisture meter (10) will indicate the temperature of the hay on the sixteen-character display (14).

Figure 5:
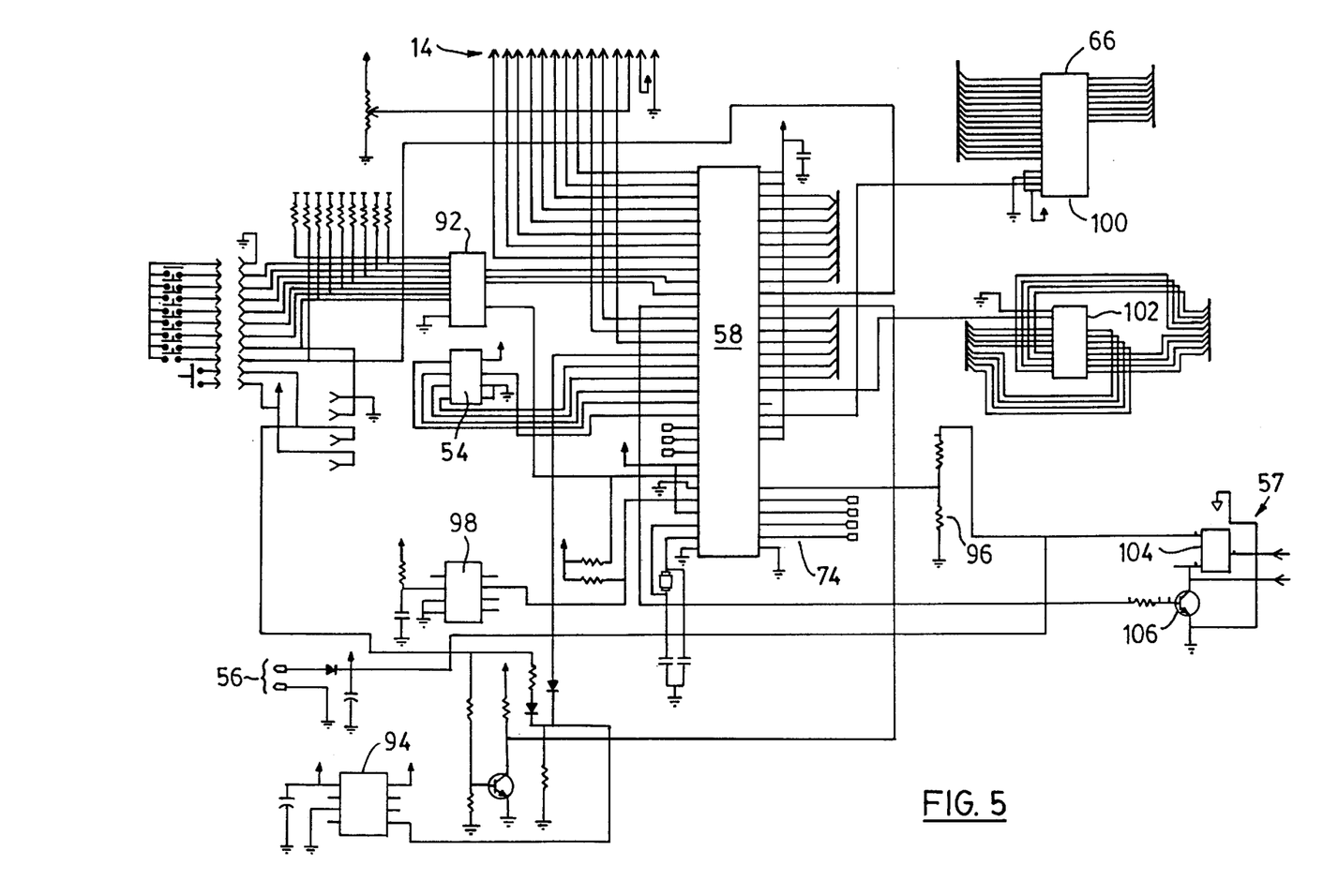
FIG. 5 is a circuit schematic of the digital electronics for the portable hay moisture tester of FIG. 1.

With additional reference to FIG. 5, the operator may elect to select and modify variables associated with the hay such as the bale type, hay cutting, hay type and hay density. This feature enables the moisture tester to more accurately determine the moisture of the hay. This feature of the invention is made possible by the storage of various bale types, cuttings, hay types and densities in the electrically erasable memory device herein using an EEPROM (54) which retains information even in the absence of power from the circuitry or even if the battery (56) powering the circuitry of is removed.

This feature of the invention is activated by depressing the 'Menu' button (58). This feature allows for modifying the choices for bale type, hay cutting, type of hay and hay density sequentially by means of depressing certain membrane switch buttons on the membrane switch control panel (16). Once the menu button (58) is activated, the sixteen character display (14) will indicate the bale type that was last selected, either round or square bale. By depressing either the 'up arrow' button (60) or the 'down arrow' button (62) the operator can toggle the bale type from round to square, or from square to round.

Once the bale type is selected, the operator can exit the menu by depressing the 'menu' button (58) again, or can proceed to the next menu item by depressing an 'enter' button (64). If either the 'enter' button (64) or the 'menu' button (58) is selected, the bale type is stored in EEPROM (54).

If the 'enter' button (64) was selected, the display (14) will indicate the hay cutting that was last selected. By depressing the 'up arrow' (60) the cutting number is increased and by depressing the 'down arrow' (62) the cutting number is decreased. The arrow keys can be continuously manipulated until the desired cutting number is displayed.

Once the cutting is selected, the operator can exit the menu by depressing the 'menu' button (58), or the next menu item may be obtained by depressing the 'enter' button (64). Again if either the 'enter' button (64) or the 'menu' button (58) is selected, the cutting number is stored in EEPROM (54).

If the 'enter' button (14) was selected, the display (14) will indicate the hay type that was last selected. By depressing the 'up arrow' or the 'down arrow', the operator may increment or decrement through the hay type selections until the hay type selection most closely matching the hay being tested is displayed. Hay type examples are: Alfalfa, Timothy, Clover, Mixed Grass, etc.

Once the hay type is selected, the operator can exit the menu by depressing the 'menu' button (58), or the next menu item may be obtained by depressing the 'enter' button (64). Again if either the 'enter' button (64) or the 'menu' button (58) is selected, the hay type selected is stored in EEPROM (54).

If the 'enter' button (64) was selected, the display (14) will indicate the hay density that was last selected. By depressing the 'up arrow' or the 'down arrow', the operator may increment or decrement through the hay density selections until the hay density selection most closely matching the hay being tested is displayed.

Once the hay density is selected, the operator can exit the menu by depressing the 'menu' button or the 'enter' button (64). Again if either the 'enter' button (64) or the 'menu' button is selected, the hay type selected is stored in EEPROM (54).

Figure 6:
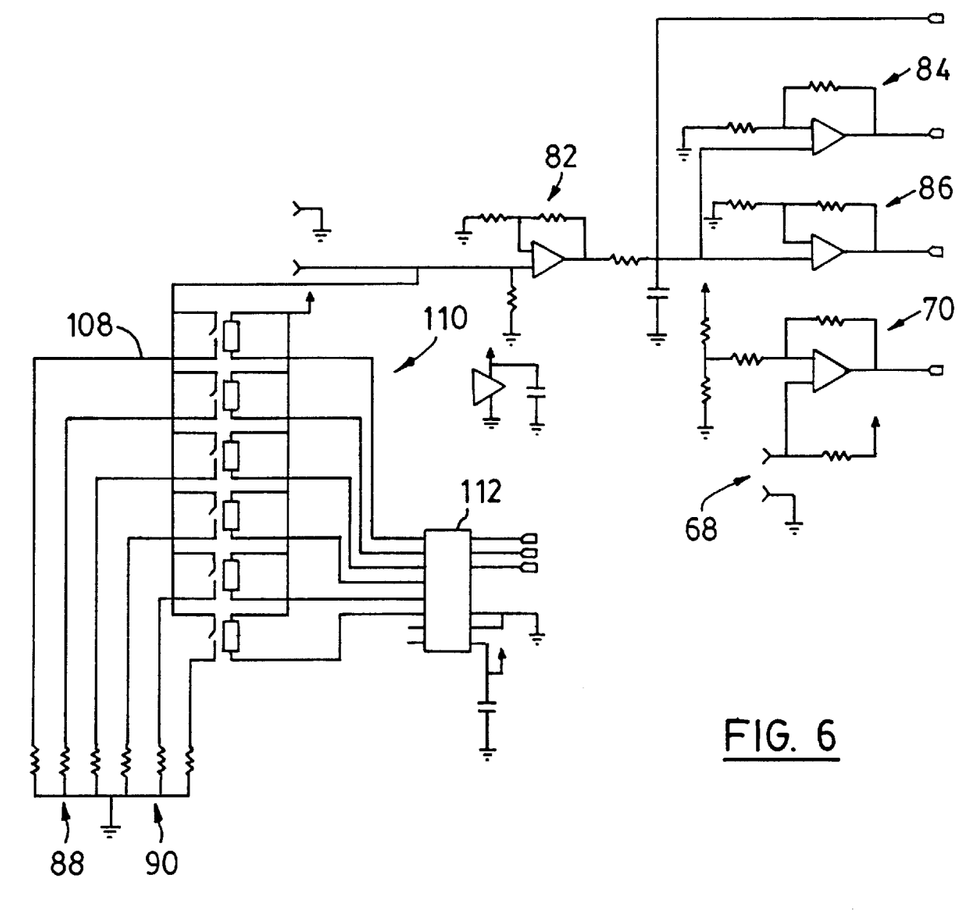
FIG. 6 is a circuit schematic of the analog electronics for the hay moisture tester of FIG. 1.

The electrical circuitry shown in FIGS. 5 and 6 has two distinct types of memory storage integrated circuits one being a Programmable Read Only Memory (66) which contains the microprocessor program instructions, the sensor signal conversion algorithm for converting the signal to moisture, the temperature compensation algorithm, and all of the other algorithms for biasing the moisture reading based on the operator selections of bale type, hay cutting, hay type and hay density. This memory device is programmed at the factory and cannot be altered by the operator.

The other memory device is the Electrically Erasable Programmable device (54) referred to as EEPROM which contains the last selected hay variable parameters chosen by the operator (i.e. the last: bale type selected, hay cutting selected, hay type selected and hay density selected). The EEPROM (54) contains information that may vary during the course of using the moisture tester and is able to retain this information in the absence of battery power.

Since there are various hay parameters that can be selected to achieve better moisture reading accuracy, the detailed, digital, full alpha-numeric text display (14) of sixteen characters and of known manufacture is used to display the menu selections, the moisture, temperature and other related messages to the operator.

Since the portable moisture tester (10) is sometimes used in low ambient light conditions, the digital display (14) is back lighted by a known light source (57) whenever a 'backlight' switch (56) is toggled on. By again depressing the 'backlight' switch (56) the backlight is toggled off. A microprocessor (58) monitors the backlight switch (56) and toggles the backlight on if it was previously off and off if it were previously on. Thus the backlight (56) under microprocessor (58) control can be toggled off or on at any time that the moisture meter (10) is on. The microprocessor (58) also sends a signal to the sixteen-character display (14) which produces a solid black dot (60) at a specific character position indicating that the backlight is activated. The dot remains on as long as the backlight is on and is off if the backlight is off. The dot (60) acts as a reminder to the operator to turn off the backlighting if it is unnecessary, thus saving on battery life by decreasing the backlight current drain on the battery.

When the operator has completed selecting the desired menu parameters related to the hay being tested, the test switch (50) is depressed to initiate the moisture testing of the hay. The moisture measuring circuitry completes the measurement under microprocessor (58) control and displays the moisture content of the hay on the sixteen-character digital display (14). In addition, the letter 'R' for round bale or 'S' for square bale is displayed reminding the operator of the last bale type selected. This feature of the present invention is important because if the wrong bale type was previously selected, the moisture reading could be less accurate. The moisture measurement may be saved to memory by depressing a memory switch (62). Subsequent tests may thus be saved and the average of these tests also saved along with the number of tests performed. The minimum moisture reading and the maximum moisture reading can be displayed on the sixteen character digital display. This statistical data will be sequentially displayed when the operator depresses the stat switch (64).

Clearing of all these statistical values can be accomplished by depressing the clear switch (61).

The temperature switch (52), when depressed, is processed by the microprocessor (58) and the microprocessor (58) sends a signal to the sixteen-character digital display (14) resulting in the display of the hay bale temperature in both degrees Fahrenheit and Celsius.

All of the membrane switches (16) are connected to the microprocessor (58) which is programmed to accomplish the mentioned functions of the various switches in a known manner obvious to computer programmers.

The overall accuracy of the portable moisture meter (10) is assured by a temperature measurement diode (68). The temperature measurement diode (68) is amplified and offset by the temperature processing amplifier (70). The output of this amplifier is then input to one of the analog to digital inputs (74) of the microprocessor (58) which mathematically calculates and biases the moisture measurement in the correct manner so as to achieve better moisture measurement accuracy.

To accomplish the moisture measurement, the probe (18) is inserted into the hay bale with the bimetal areas and insulator area (80) portions of the probe acting as a single cell battery. Amplifiers (82, 84, 86) of three different gains, feed the amplified cell voltage to the appropriate analog to digital inputs (74) of the microprocessor (58). Under microprocessor control, one of two different 'banks' of resistive loads (88) and (90) are sequentially switched across the probe (18) causing the cell voltage to drop as a function of load.

Figure 4:
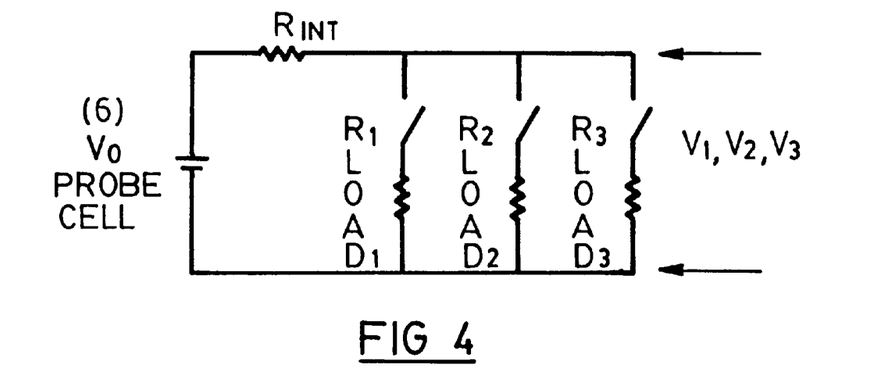
FIG. 4 is a circuit schematic of the calibration circuit used to develop the graph shown in FIG. 3.

FIG. 4 demonstrates a basic equivalent circuit for the measurement phenomena showing the probe cell, the probe cell's internal resistance Rint, and the three load resisters R1, R2, R3 of a given bank. For a moisture measurement, first the open cell voltage, V0, is read and retained by the microprocessor (58) Next, R1 is switched in across the cell. This results in a current flowing through the internal resistance of the cell and through the load resister R1. The result is a voltage drop across the internal resistance of the cell. The higher the moisture of the hay, the less internal resistance of the cell and the less voltage that is dropped across this internal resistance. The three different load resisters enable the moisture meter (10) to achieve a better dynamic moisture measurement range than using a single load resister.

V0 is the initial open cell voltage which is generated as soon as the probe is inserted into the bale. As soon as the moisture test button (50) is depressed, this voltage is read by the microprocessor (58) by virtue of the analog to digital inputs (74). This voltage, V0, is retained in the internal SRAM of the microprocessor (58). Then sequentially the resistive loads of either bank one (88) or bank two (90) are switched in across the probe cell (18) from less load to more load. The particular bank that is switched in is determined by the bale type selected by the operator, either round bales or square bales. In any event, immediately after processing the open cell voltage, V0 the microprocessor switches the first load resistor across the probe cell (18) causing the open cell voltage, V0, to drop to some other level, V1 due to the voltage drop across the internal resistance of the probe cell (18). The microprocessor (58) again performs analog to digital conversions on this voltage level and retains this voltage level, V1, in internal SRAM. The first load is removed and the second load, of smaller resistance then the first, is then switched in across the cell (18) causing the cell voltage to drop to a third level, V2. Once again, this voltage level is read and retained in SRAM. Then the second load is removed and a third load, being less resistance than the second, is switched in causing the voltage to drop to a third level, V3. This voltage level is read and retained in SRAM.

The change in voltage from V0 to V1, V0 to V2, and V0 to V3 is inversely proportional to the moisture within the hay bale. If the bale is wet, the bale acts as a better electrolyte and thus makes the probe cell (18) function as a stronger battery with less internal resistance than if the bale was of drier moisture.

When the bale is very wet, the battery created by the bimetallic probe and the hay bale is strong and has very little internal resistance. Then when the first resistor load is placed across the cell (18) a current is generated and flows from the battery cell through the battery cell's internal resistance and through the first load resistor. Since the internal resistance of the cell (18) is small compared to the load resistance, very little voltage is dropped across the internal cell resistance and therefore the voltage level of V1 is almost the same as V0. Then the first load is removed and the second load is placed across the cell. Again a current is generated and flows from the battery cell through the battery cell's internal resistance and through the second load resistor. Since this resistance is smaller then the first load resistance, a greater current flows and therefore, V2 will be of a lower amplitude than V0 or V1. The sequence is again repeated for the third load. By mathematically processing the voltage levels, V0, V1, V2, and V3, the microprocessor calculates the correct moisture.

As best seen in the FIG. 5 schematic, the microprocessor (58) or digital section of the circuit of the present invention is an intelligent controller that contains internal static ram (SRAM), an internal eight bit Analog to Digital (A/D) converter and numerous programmable input/output ports (I/O ports). The membrane switches are read by the microprocessor (58) by means of decoder I.C. (92). The sixteen-character digital display (14) is controlled by the microprocessor (58) via a parallel input/output port of the said microprocessor (58).

The battery is connected to a regulator (94) and is monitored by the microprocessor (58) via the said microprocessor's analog to digital converter through a simple resistor voltage divider (96). A power on reset I.C. (98) assures that the microprocessor (58) activates properly when battery power is first applied. The EEPROM is controlled directly by the microprocessor (58) by I/O lines of the said microprocessor (58). The program memory as well as the hay variable selections are contained in the PROM (66). A bus transceiver (102) interfaces the PROM (66) and the microprocessor (58). The backlight for the sixteen character digital display (14) is driven by a backlight driver module (104) which is enabled/disabled via a transistor (106) circuit which is controlled by a microprocessor (58) I/O line.

In the analog section of the present invention seen in FIG. 6, the bimetallic probe (18) is connected to a buffer amplifier (82). The output from this amplifier (82) is amplified to two distinct gains via the two additional amplifiers (84, 86). The outputs from all three of these amplifiers are connected to the A/D inputs (108) of the microprocessor (58). The various load resistors (88,90) are connected across the probe (18) via a series of relays (110). The relays (110) are energized by a BCD to 1 of 7 decoder I.C. (112), which is controlled by I/O lines (108) of the microprocessor (58).

From the foregoing it will be seen that the present invention provides a portable hay moisture tester having a wide range of moisture measurements including measurements above 40% moisture and also providing compensation for differing hay types and hay bale conditions and configurations.

It will be understood that certain obvious operational explanations as well as additions and modifications have been deleted herein for the sake of conciseness and readability but are intended to be within the scope of the following claims.

I claim:

1. A portable moisture meter for measuring the moisture of a hay bale comprising:
   a tubular shaped bimetallic probe separated by an insulator for easy inserting an indicated distance into the hay bale to act as a single cell battery in which the internal resistance is inversely proportional to the moisture in the hay;
   an electronic circuit connected to said bimetallic probe for converting the internal resistance of said probe to a moisture measurement within the hay bale by a predetermined algorithm and
   a self contained portable housing containing said electronic circuit therein and having said bimetallic probe extending there from and being electronically connected to said electronic circuit within said housing.

2. A meter as set for in claim 1 including biasing means for compensating the hay moisture measurement for the round or square shape of the hay bales.

3. A meter as set forth in claim 2 including a microprocessor which sends a character signal to the sixteen character display to indicate if the bale type selected by the operator is round or square.

4. A meter as set forth in claim 1 including biasing means for compensating the hay moisture measurement for leaf to stem ratio as determined by the cutting of the hay.

5. A meter as set forth in claim 1 including biasing means for compensating the hay moisture measurement for the packing density of the hay bale.

6. A meter as set forth in claim 5 including an EEPROM for retaining the bale density when battery power is removed or turned off.

7. A meter as set forth in claim 1 including compensating means for compensating the hay measurement for the type of hay being tested.

8. A meter as set forth in claim 7 including an EEPROM for retaining the last bale type configuration tested whenever the power is turned off from the meter.

9. A meter as set forth in claim 8 including bias means for biasing the signal based on the hay bale type being tested.

10. A meter as set forth in claim 9 including bias means for biasing the signal based on the bale cutting being tested.

11. A meter as set forth in claim 10 including a bias means for biasing the signal based on the bale density being tested.

12. A meter as set forth in claim 11 including a bias means for biasing the signal based on the type of hay being tested.

13. A meter as set forth in claim 7 including an EEPROM for retaining the bale cutting when battery power is removed or turned off.

14. A meter as set forth in claim 1 including a temperature sensor mounted within said bimetallic probe for compensating the hay measurement for the temperature of the hay bale tested.

15. A meter as set forth in claim 14 including computer means having a microprocessor connected to said temperature sensor to calculate the temperature of the hay being moisture tested.

16. A temperature compensation assembly as set forth in claim 15 including an EPROM connected to said microprocessor and having an empirically derived temperature compensation calculation accessible by said microprocessor for modifying the measurement of said moisture measuring probe.

17. A meter as set forth in claim 1 including a sixteen character digital, alphanumeric, full text, display.

18. A meter as set forth in claim 1 including a backlight selectively actuated to illuminate said sixteen-character display.

19. A meter as set forth in claim 18 including an indicator on said sixteen-character display for indicating that said backlight is "on".

20. A meter as set forth in claim 1 including computer means having a PROM with a listing of bale types and a microprocessor connected to said PROM having a listing of bale cuttings and a microprocessor connected to said PROM and said sixteen character display to sequentially display a series of bale type selections in response to a switch signal from said meter.

21. A meter as set forth in claim 20 wherein said computer means includes a PROM having a listing of bale types and a microprocessor connected to said PROM and said sixteen character display to sequentially display a series of bale type cutting selections in response to a switch signal from said meter.

22. A meter as set forth in claim 21 wherein said computer means includes a PROM having a listing of bale densities and a microprocessor connected to said PROM and said sixteen character display to sequentially display a series of bale density selections in response to a switch signal from said meter.

23. A meter as set forth in claim 22 wherein said computer means includes a PROM having a listing of types of hay and a microprocessor connected to said PROM and said sixteen character display to sequentially display a series of hay selections in response to a switch signal from said meter.

24. A meter as set forth in claim 23 wherein said sixteen character displays the signal established by said computer means as modified by said bias means in response to a "TEST" switch signal.

25. A meter as set forth in claim 1 wherein said bimetallic probe includes bimetal separated by an insulator which is used as the moisture measuring sensor.

26. A meter as set forth in claim 1 wherein said probe has one or more markings along its length for indicating the depth of penetration of the probe into the hay bale.

27. A method of measuring the moisture content of a bale of hay comprising the steps of:
   providing a bimetallic probe forming a single cell battery;
   inserting said probe into the hay bale a predetermined distance to allow the hay and the moisture therein to act as electrolytes to set up a cell resistance proportional to the moisture content of the hay bale;
   calculating the hay bale moisture according to calculated relationship between cell resistance and moisture content; and
   compensating the calculated hay moisture measurement for leaf to stem cutting ratio of hay forming the hay bale.

28. A method as set forth in claim 27 including compensating the calculated hay moisture measurement for temperature, bale configuration, type of hay, and cutting.

* * * * *